United States Patent [19]
Wolfson et al.

[11] Patent Number: 5,854,077
[45] Date of Patent: Dec. 29, 1998

[54] CONTINUOUS MEASUREMENT OF PARTICULATE NITRATE

[75] Inventors: Jack Mikhail Wolfson, Jamaica Plain; Petros Koutrakis, Wellesley, both of Mass.

[73] Assignee: President and Fellows of Harvard College, Cambridge, Mass.

[21] Appl. No.: 658,141

[22] Filed: Jun. 4, 1996

[51] Int. Cl.[6] ........................... G01N 33/00; B01D 46/00
[52] U.S. Cl. ..................... 436/110; 436/100; 436/113; 436/148; 422/55; 422/61; 422/83; 422/88; 422/93; 55/270; 55/485; 55/486; 95/285
[58] Field of Search ................... 422/52, 55, 61, 422/83, 88, 93; 55/270, 485, 486; 95/285; 436/100, 110, 113, 148, 172

[56] References Cited

PUBLICATIONS

Brauer et al., "Measurements of Nitrous Acid Inside Two Research Houses," *Environmental Science & Technology* 24:1521–1527 (1990).

Koutrakis et al., "Evaluation of an Annular Denuder/Filter Pack System to Collect Acidic Aerosols and Gases," *Environmental Science & Technology* 22:1463–146 (1988).

Klockow et al., "Determination of Nitric Acid and Ammonium Nitrate by Means of Computer Controlled Thermodenuder System," *Atmospheric Environment* 23:1131–1138 (1989).

Koutrakis et al., "Determination of Aerosol Strong Acidity Losses Due to Interactions of Collected Particles: Results From Laboratory and Field Studies," *Atmospheric Environment* 26A:987–995 (1992).

Wendt et al., "Continuous monitoring of atmospheric nitric oxide and nitrogen dioxide by chemiluminescence," in *Methods of Air Sampling and Analysis*, J.P. Lodge Jr. editor, Lewis Publishers, Chelsea, Michigan, pp. 415–421 (1989).

*Primary Examiner*—Ponnathapura Achutamurthy
*Assistant Examiner*—P. Ponnaluri
*Attorney, Agent, or Firm*—Lyon & Lyon LLP

[57] ABSTRACT

A method for continuously measuring particulate nitrate in a gas sample, comprising the steps of passing the gas sample through an inertial impactor with a 50% cut off at 2.5 microns, removing ambient pollutant gases from the gas with diffusion denuders, passing the gas through a first path so as to contact the gas with a coated filter so as to convert particulate nitrate to nitric acid vapor or passing the gas through a second path so as to contact the gas with coated filters to trap particulate nitrate and ammonia, and measuring nitric acid vapor and residual ambient pollutant gases produced from the first path and residual ambient pollutant gases produced from the second path with a chemiluminescent monitor, the difference in the signal produced from the gases from the two paths being a measurement of the particulate nitrate in the gas sample.

8 Claims, 1 Drawing Sheet

CONTINUOUS MEASUREMENT OF PARTICULATE NITRATE

BACKGROUND OF THE INVENTION

This invention relates to the monitoring of atmospheric particulate nitrate.

The following description of the background of the invention is provided to aid in the understanding of the invention, but is not admitted to be prior art to the invention.

Brauer et al., *Environ. Sci. Technol.* 24:1521, 1990 disclose a method for the continuous measurement of the sum of nitrous acid vapor and nitric acid vapor, which does not allow for these gases to be distinguished from each other.

Koutrakis et al., *Environ. Sci. Technol.* 22:1463, 1988 disclose an integrated sampling method (Harvard/EPA Annular Denuder System (HEADS)) which is designed to measure various atmospheric components including particulate nitrate. The method provides a non-quantitative conversion of particulate nitrate to nitric acid vapor by collection of atmospheric fine particles on a Teflon filter, with a sodium carbonate-coated filter downstream to collect nitric acid vapor produced by volatization of ammonium nitrate and by the reaction of ammonium nitrate with acidic sulfate particles. Koutrakis et al. further disclose a method designed to measure the amount of loss of acidity from acidic sulfate particles collected on the Teflon filter, with the loss caused by neutralization of acidic sulfate with particulate ammonium nitrate collected on the same filter.

Klockow et al., *Atmospheric Environment* 23:1131, 1989 disclose thermodenuder systems for the discontinuous measurement of nitric acid vapor and ammonium nitrate.

Koutrakis et al., *Atmospheric Environment* 26A:987, 1992 disclose that independent collection of artificial particles of acidic sulfate and ammonium nitrate on the same Teflon filter resulted in the production of gaseous nitric acid, which was collected downstream on a sodium carbonate-coated glass fibre filter.

Wendt et al., "Continuous monitoring of atmospheric nitric oxide and nitrogen dioxide by chemiluminescence" in Methods of Air Sampling and Analysis, editor, J. P. Lodge Jr., Lewis Publishers, Chelsea, Mich., pp 415–421 (1989), disclose a continuous chemiluminescent $NO_x$ method.

SUMMARY OF THE INVENTION

The present invention concerns measurement of particulate nitrate continuously, in situ. This method can be summarized as follows: first, coarse particles are removed with an impactor; second, diffusion denuders are used to remove ambient pollutant gases; third, the gas containing all of the fine particles passes through a coated glass fibre filter (which converts the particle nitrate to nitric acid vapor (gas)); fourth, nitric acid vapor is measured continuously by a chemiluminescent $NO_x$ monitor.

The advantages of the current invention are numerous. This technique allows continuous real time quantitative measurements of particulate nitrate for ambient air. With the most sensitive commercially available version of the chemiluminescent $NO_x$ monitor, the method of the present invention enables the measurement of a lower quantifiable limit (LQL) of 0.26 $\mu g/m^3$ nitrate for a one hour average. This continuous system provides direct measurements of particulate nitrate and is an improvement over all integrated methods using filters, which have potential losses associated with vaporization of particle nitrate. Because most of the ambient pollutant gases are removed by the denuders, the sensitivity for nitric acid vapor is tremendously improved, compared to previously used integrated filter methods.

Thus, in a first embodiment the invention features a method for continuously measuring particulate nitrate in a gas sample, comprising the steps of passing the gas sample through an inertial impactor with a 50% cut off at 2.5 microns, removing ambient pollutant gases from the gas with diffusion denuders, passing the gas through a first path so as to contact the gas with a coated filter so as to convert particulate nitrate to nitric acid vapor or passing the gas through a second path so as to contact the gas with coated filters to trap particulate nitrate and ammonia, and measuring nitric acid vapor and residual ambient pollutant gases produced from the first path and residual ambient pollutant gases produced from the second path with a chemiluminescent monitor, the difference in the signal produced from the gases from the two paths being a measurement of the particulate nitrate in the gas sample.

By "gas sample" is meant atmospheric or ambient air.

By "passing the gas sample through an inertial impactor with a 50% cut-off at 2.5 microns" is meant that 50% of the particles that are 2.5 microns in diameter are removed from the gas sample and 50% of the 2.5 micron particles pass through the inertial impactor. For particles less than 2.5 microns in diameter a greater fraction pass through the inertial impactor and for particles greater than 2.5 microns in diameter a smaller fraction pass through the inertial impactor.

By "gas" is meant a gas sample from which either particles or pollutant vapors have been partially or completely removed and includes both vapor and suspended particles or vapor without the presence of particles.

By "ambient pollutant gases" is meant to include gases such as nitric oxide, nitrogen dioxide, nitric acid, nitrous acid, ammonia and peroxyacetylnitrate (PAN), which are typically present in atmospheric or ambient air.

By "removing ambient pollutant gases" is meant removing at least 90%, preferably 99% or greater of the ambient pollutant gases from the gas, without removing small particles, so as to achieve a maximum sensitivity in the measurement of nitrate of 0.26 $\mu g/m^3$ for a one hour average.

By "convert particulate nitrate to nitric acid vapor" is meant use of an acid-coated filter which allows for the particulate nitrate to contact the filter and be quantitatively and continuously converted to nitric acid vapor. It is necessary to have a large excess of acid for quantitative conversion, in order to completely react with all of the particulate nitrate as it is collected. Continuous conversion is conversion of particulate nitrate to nitric acid vapor when the particulate nitrate comes in contact with the coated filter. A non-volatile strong acid must be used for coating the filter, preferably sulfuric acid.

By "trap particulate nitrate and ammonia" is meant collecting on the filters at least 99% of the particulate nitrate and ammonia in the gas. In order to have no more than a 1% error in the particulate nitrate measurement, 99% of the particle phase nitrate must be collected and 99% of the ammonia must be collected on the appropriate filters.

"Residual ambient pollutant gases" are those ambient pollutant gases that have not been removed by the diffusion denuders and can be measured by the chemiluminescent $NO_x$ method and thus interfere with the measurement of nitric acid vapor generated from particulate nitrate.

In preferred embodiments, the diffusion denuders are a denuder coated with sodium carbonate and a denuder coated with potassium permanganate; the filter to convert particulate nitrate to nitric acid vapor is coated with sulfuric acid and the filters to trap particulate nitrate and ammonia are a filter coated with sodium carbonate to trap particulate nitrate and a filter coated with citric acid to trap ammonia.

The summary of the invention described above is non-limiting and other features and advantages of the invention will be apparent from the following description of the preferred embodiments, and from the claims.

DESCRIPTION OF THE PREFERRED EMBODIMENTS

Figure 1:
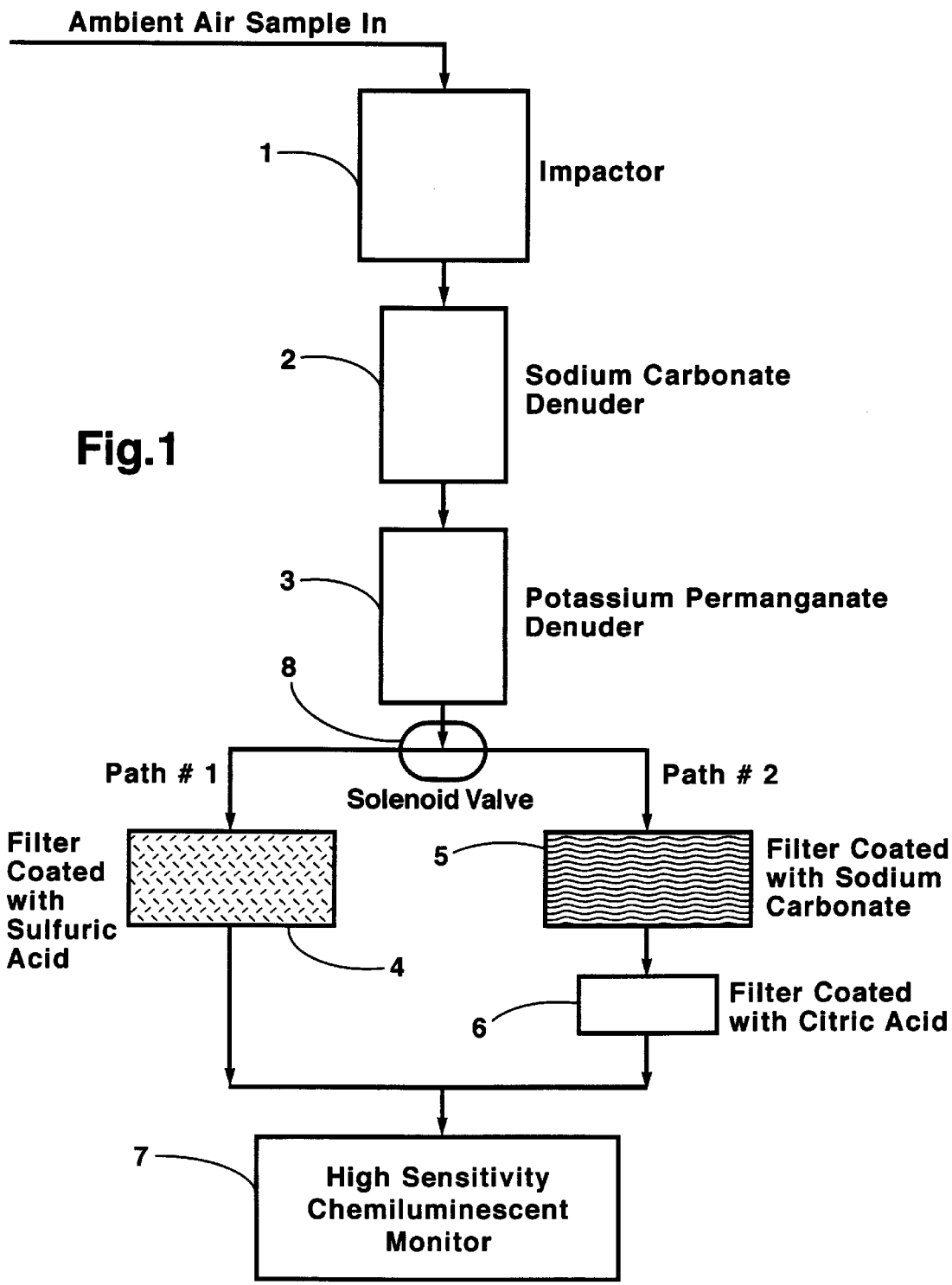

The drawing will briefly be described.

Drawing

FIG. 1 is a schematic representation of the components required to perform the method for continuous monitoring of particulate nitrate. There are eight important features: an impactor 1 to remove coarse particles (50% cut-off at 2.5 microns); a sodium carbonate denuder 2 to remove gaseous nitric acid and nitrous acid; a potassium permanganate denuder 3 to remove nitric oxide, nitrogen dioxide, ammmonia and peroxyacetylnitrate; a filter coated with sulfuric acid 4 to quantitatively convert particulate nitrate to nitric acid vapor; a filter coated with sodium carbonate 5 to trap particulate nitrate; a filter coated with citric acid 6 to collect ammonia; and a chemiluminescent monitor 7 to detect nitric acid vapor and residual ambient pollutant gases. A solenoid valve 8 allows for switching between the two paths, one path containing the filter coated with sulfuric acid 4 and the second path containing the filter coated with sodium carbonate 5 and the filter coated with citric acid 6.

The method entails several steps, which will be described. In a first step, coarse particles are removed by an inertial impactor. The sample air is accelerated through a jet which creates enough inertia to cause particles larger than 2.5 $\mu$m to impact onto a flat surface. The particles which hit the surface stick to it, and are removed from the air sample, while the smaller particles do not have enough momentum to impact, and are carried by the gaseous portion of the air past the impaction surface. The result is a gas which has the same concentration of gases and particles smaller than 2.5 $\mu$m as the original sample air, but almost all of the larger particles (greater than 2.5 microns in diameter) are removed.

Most of the particles larger than 2.5 $\mu$m must be removed from the system which is directed toward the measurement of only fine particle nitrate (less than 2.5 $\mu$m in diameter). It is only the smaller particles which contribute to decreased visibility, which is the primary concern of potential users of this method. A secondary reason for removing the particles which are larger than 2.5 $\mu$m is that they usually contain earth crustal materials, which are alkaline. The measurement method for nitrate uses a sulfuric acid-coated filter to convert particle nitrate to gas phase nitric acid (see below). The alkaline particles could use up the sulfuric acid more quickly if they were not removed from the air sample.

In a second step, ambient pollutant gases are removed by the sequential passage through two diffusion denuders, coated with sodium carbonate and potassium permanganate, respectively. The fine particles pass through unaltered (because the residence time in the denuders is short, there is no volatilization of ammonium nitrate particles, as was shown by Koutrakis et al., 1992, supra). While it is relatively easy to selectively remove gaseous nitric acid and nitrous acid using a sodium carbonate-coated diffusion denuder, removal of nitric oxide requires a strong oxidant such as potassium permanganate. Potassium permanganate will also effectively removes the other dominant nitrogen oxide species, nitrogen dioxide, ammonia, and peroxyacetylnitrate, which can be partially converted to nitric oxide by the catalytic converter of the chemiluminescent monitor (see below). Because potassium permanganate reacts with many other pollutant gases, including many volatile organics, the efficiency of this denuder for removing the nitrogen oxide species and ammonia could decrease slowly with time. Passage of a relatively small amount of these gaseous species through the denuder system would cause a significant positive interference with the measurement of particulate nitrate.

To overcome this limitation, in a third step the system is designed so that the gas which has passed through the diffusion denuders will switch back and forth between two paths prior to entering the chemiluminescent monitor.

The first path contains a sulfuric acid-coated glass fiber filter. The gas containing the fine particles passes through a sulfuric acid-coated glass fiber filter, which converts all particle nitrate to nitric acid vapor: sulfuric acid+2 ammonium nitrate→ammonium sulfate+2 nitric acid (vapor). Measurement of the gas from this path will allow the determination of the amount of particulate nitrate plus any residual ambient interfering pollutant gases that were not trapped by the denuders. It is necessary to heat the tubing between the sulfuric acid-coated filter and the chemiluminescent monitor (see below) to keep the nitric acid vapor from being lost on the walls of the tubing.

The second path has filters to remove particulate nitrate and ammonia. One filter is a sodium carbonate-coated filter to trap the particulate nitrate, and simultaneously prevent passage of any nitric acid vapor which would otherwise volatilize from the collected nitrate particles. A second filter is a citric acid-coated filter provided after the sodium carbonate filter. The citric acid filter will remove gaseous ammonia produced by reaction of ammonium nitrate particles with sodium carbonate. If the ammonia was not removed, it would be detected by the chemiluminescent monitor, thus causing an artifact in the background measurement. Passage of the sample gas through the second path allows for the subsequent measurement of only the residual ambient pollutant gases (nitric acid, nitrous acid, nitric oxide, nitrogen dioxide, ammonia, and peroxyacetylnitrate).

In a fourth step, nitric acid vapor and residual ambient pollutant gases are passed directly into the converter of the chemiluminescent $NO_x$ monitor, and are subsequently measured as nitric oxide (Wendt et al., 1989). The difference in signal for the chemiluminescent monitor generated from the measurement of gas from the two paths (path 1 and path 2) will be due only to the particle nitrate in the ambient atmosphere. An added benefit of the two path difference system is that it overcomes baseline drift in the detector of the chemiluminescent monitor, improving the long-term sensitivity of the method.

Other embodiments are within the following claims.

We claim:

1. Method for continuously measuring particulate nitrate in a gas sample, comprising the steps of:

passing said gas sample through an inertial impactor with a 50% cut-off at 2.5 microns, removing ambient pollutant gases from said gas with diffusion denuders, passing said gas through a first path so as to contact said gas with a coated filter so as to convert particulate nitrate to nitric acid vapor or passing said gas through a second path so as to contact said gas with coated filters to trap particulate nitrate and ammonia, and measuring nitric acid vapor and residual ambient pollutant gases produced from said first path and residual ambient pollutant gases produced from said second path with a chemiluminescent monitor, the difference in the signal produced from the gases from the two paths being a measurement of the particulate nitrate in said gas sample.

2. The method of claim 1, wherein said diffusion denuders are a denuder coated with sodium carbonate and a denuder coated with potassium permanganate.

3. The method of claim 1, wherein said coated filter which converts particulate nitrate to nitric acid vapor is a filter coated with sulfuric acid and said coated filters to trap particulate nitrate and ammonia comprise:

a filter coated with sodium carbonate to trap particulate nitrate, and a filter coated with citric acid to trap ammonia.

4. Method for continuously measuring particulate nitrate in a gas sample, comprising the steps of:

passing said gas sample through an inertial impactor with a 50% cut-off at 2.5 microns, removing ambient pollutant gases from said gas with a diffusion denuder coated with sodium carbonate and a diffusion denuder coated with potassium permanganate, passing said gas through a first path so as to contact said gas with a sulfuric acid coated filter so as to convert particulate nitrate to nitric acid vapor or passing said gas through a second path so as to contact said gas with a sodium carbonate coated filter to trap particulate nitrate and a citric acid coated filter to trap ammonia, and measuring nitric acid vapor and residual ambient pollutant gases produced from said first path and residual ambient pollutant gases produced from said second path with a chemiluminescent monitor, the difference in signal produced from the gases from the two paths being a measurement of the particulate nitrate in said gas sample.

5. A device for the continuous measurement of particulate nitrate comprising:

an inertial impactor with a 50% cut-off at 2.5 microns;

diffusion denuders for removing ambient pollutant gases;

a first path for gas comprising a coated filter to convert particulate nitrate to nitric acid vapor;

a second path for gas comprising filters to trap particulate nitrate and ammonia; and a chemiluminescent monitor to measure nitric acid vapor and residual ambient pollutant gases from the first path, and residual ambient pollutant gases from the second path, the difference in the signal produced from the gases from the two paths being a measurement of the particulate nitrate in said gas sample.

6. The device of claim 5, wherein said filters to trap particulate nitrate and ammonia are a filter coated with sodium carbonate to trap particulate nitrate and a filter coated with citric acid to trap ammonia.

7. A device for the continuous measurement of particulate nitrate comprising:

an inertial impactor with a 50% cut-off at 2.5 microns;

diffusion denuders for removing ambient pollutant gases, wherein said diffusion denuders are a denuder coated with sodium carbonate and a denuder coated with potassium permanganate;

a first path for gas comprising a coated filter to convert particulate nitrate to nitric acid vapor;

a second path for gas comprising filters to trap particulate nitrate and ammonia; and a chemiluminescent monitor to measure nitric acid vapor and residual ambient pollutant gases.

8. A device for the continuous measurement of particulate nitrate comprising:

an inertial impactor with a 50% cut-off at 2.5 microns;

diffusion denuders for removing ambient pollutant gases;

a first path for gas comprising a coated filter to convert particulate nitrate to nitric acid vapor, wherein said coated filter to convert particulate nitrate to nitric acid vapor is coated with sulfuric acid;

a second path for gas comprising filters to trap particulate nitrate and ammonia; and a chemiluminescent monitor to measure nitric acid vapor and residual ambient pollutant gases.

* * * * *